United States Patent
Daley et al.

(10) Patent No.: US 9,173,850 B2
(45) Date of Patent: Nov. 3, 2015

(54) 4-METHYLPYRAZOLE FORMULATIONS

(75) Inventors: Thomas E. Daley, San Mateo, CA (US); Kathy Powell, Cary, NC (US); Olga Jarzebinski, Loveland, OH (US)

(73) Assignee: RAPTOR PHARMACEUTICALS INC., Novato, CA (US)

( * ) Notice: Subject to any disclaimer, the term of this patent is extended or adjusted under 35 U.S.C. 154(b) by 730 days.

(21) Appl. No.: 13/497,166

(22) PCT Filed: Dec. 6, 2010

(86) PCT No.: PCT/US2010/059065
§ 371 (c)(1),
(2), (4) Date: May 18, 2012

(87) PCT Pub. No.: WO2011/071805
PCT Pub. Date: Jun. 16, 2011

(65) Prior Publication Data
US 2012/0244217 A1    Sep. 27, 2012

Related U.S. Application Data

(60) Provisional application No. 61/267,389, filed on Dec. 7, 2009.

(51) Int. Cl.
*A61K 9/48* (2006.01)
*A61K 31/415* (2006.01)

(52) U.S. Cl.
CPC ............. *A61K 9/4858* (2013.01); *A61K 31/415* (2013.01)

(58) Field of Classification Search
CPC ........................... A61K 9/4858; A61K 31/415
See application file for complete search history.

(56) References Cited

U.S. PATENT DOCUMENTS

| | | | |
|---|---|---|---|
| 6,120,806 A | 9/2000 | Whitmire | |
| 6,197,787 B1* | 3/2001 | Franson et al. | 514/313 |
| 2005/0069587 A1* | 3/2005 | Modi et al. | 424/473 |
| 2005/0147565 A1 | 7/2005 | Sequeira et al. | |
| 2008/0021083 A1* | 1/2008 | Daley | 514/406 |

OTHER PUBLICATIONS

Dial et al., Efficacy of 4-methylpyrazole for treatment of ethylene glycol intoxication in dogs, 1994, American Journal of Veterinary Research, 55(12):1762-70.*
ISA/US, PCT International Search Report dated Mar. 2, 2011 for PCT/US2010/059065.
ISA/US, PCT Written Opinion dated Mar. 2, 2011 for PCT/US2010/059065.
Feierman et al., "Increased Sensitivity of the Microsomal Oxidation of Ethanol . . ." Biochemical Pharmacology, Oct. 1987, vol. 36, No. 19, pp. 3277-3282.
Lindros et al., "A Simple Procedure Using 4-Methylpyrazole for Developing Tolerance and Other Chronic Alcohol Effects," Alcohol, 1984, vol. 1, Iss. 2, pp. 145-150.

* cited by examiner

*Primary Examiner* — Jane C Oswecki
(74) *Attorney, Agent, or Firm* — Marshall, Gerstein & Borun LLP

(57) ABSTRACT

Provided herein are 4-methylpyrazole (4-MP) formulations, stable under storage conditions of up to about 55° C.

20 Claims, No Drawings

4-METHYLPYRAZOLE FORMULATIONS

CROSS REFERENCE

This application is a U.S. National Stage filing under 35 U.S.C. §371 of International Application No. PCT/US2010/059065, filed Dec. 6, 2010, which claims the benefit of U.S. Provisional Patent Application No. 61/267,389, filed Dec. 7, 2009, the contents of each of which applications are incorporated herein by reference in their entireties.

1. TECHNICAL FIELD

Provided herein are 4-methylpyrazole (4-MP) formulations, stable under storage conditions of up to about 55° C.

2. BACKGROUND OF THE INVENTION

4-Methylpyrazole (also known as fomepizole or 4-MP) inhibits alcohol dehydrogenase (ADH), an enzyme that oxidizes alcohols as part of a two-step metabolic removal pathway in which ethanol is oxidized by ADH to acetaldehyde, which is in turn oxidized by aldehyde dehydrogenase (ALDH) to acetic acid. 4-MP has been approved by the U.S. Food and Drug Administration for the treatment of ethylene glycol or methanol poisoning. See, e.g., Scalley et al., *American Family Physician* 2002, 66, 807-812. This approved use of 4-MP requires high dose ranges, e.g., 20 mg/kg body mass initial dose, following by additional doses of 15 mg/kg every 12 hours, which are administered intravenously under the care of a physician.

Administration of doses of 4-MP below 10 mg/kg has been shown to be effective in treating ethanol intolerance or symptoms of aldehyde accumulation in subjects with reduced or absent ALDH activity who have consumed alcohol.

Patient compliance, for instance, with regard to administration of doses of 4-MP used to treat ethanol intolerance, could be improved by the development of formulations of 4-MP suitable for self-administration, in particular, oral administration. Further, it would be advantageous to have available solid formulations of 4-MP suitable for administration to subjects. Solid formulations are less prone to spillage and/or leakage than liquid formulations, are easier to package, and are easier to self-administer.

Preparation of solid formulations of 4-MP for administration to subjects that remain stable under storage conditions has proved difficult.

Thus, solid formulations comprising 4-MP, optionally in a unit dosage form, which are stable under storage conditions are sought.

3. SUMMARY OF THE INVENTION

Provided herein are formulations comprising 4-methylpyrazole (4-MP). In certain embodiments, the formulations provided herein are storage stable. Typically, formulations provided herein are suitable for oral administration.

In one aspect, provided herein are formulations comprising 4-MP, or a physiologically acceptable salt form thereof, and an excipient.

In certain embodiments, the formulations are in a solid form. In certain embodiments, the formulations are in a solid form at temperatures of from at least 25° C. to up to about 40° C. In certain embodiments, the formulations are in a solid form at temperatures of up to about 35° C. In certain embodiments, the formulations are in a solid form at temperatures of up to about 30° C.

In certain embodiments, the excipient is a polyethylene glycol. In certain embodiments, the polyethylene glycol has a total weight average molecular weight of from about 5000 to about 10,000. In certain embodiments, the excipient is PEG 8000. In certain embodiments, the formulations further comprise one or more additional excipients. In certain embodiments, the additional excipient is a surfactant. In certain embodiments, the additional excipient is selected from the group consisting of Capryol 90® and Transcutol®.

In certain embodiments, the formulations are provided as a unit dosage.

In certain embodiments, the unit dosage is in the form of a tablet or a capsule. In certain embodiments, the unit dosage is in the form of a capsule. In certain embodiments, the capsule comprises hard gelatin.

In certain embodiments, the unit dosage comprises about 10 mg 4-MP.

In certain embodiments, the unit dosage comprises about 100 mg 4-MP.

In certain embodiments, the formulations are physically and/or chemically stable for 8 months or more at room temperature and at relative humidities of up to about 60%±5%. For example, in certain embodiments, the formulation is in the unit dosage form of a capsule and displays no deformity, breakage, or leakage of contents, and retention of at least about 90% content of active pharmaceutical unit (i.e., 4-MP) when stored at room temperature and at relative humidities of up to about 60%±5% for 8 months or more.

In certain embodiments, the formulations are suitable for oral administration in a human.

In another aspect, provided herein are hard gelatin capsules encapsulating 4-MP, or a physiologically acceptable salt form thereof, and an excipient.

In certain embodiments, the hard gelatin capsules retain physical integrity when stored for 8 months or more at room temperature and at relative humidities of up to about 60%±5%. For example, in certain embodiments, the capsules display no deformity, breakage, or leakage of contents, when stored at room temperature and at relative humidities of up to about 60%±5% for 8 months or more. In certain embodiments, the excipient in the hard gelatin capsules is PEG 8000. In certain embodiments, the contents of the hard gelatin capsules are in a solid form.

In another aspect, provided are methods of administration of 4-MP comprising the formulations provided herein.

4. TERMINOLOGY

Generally, the nomenclature used herein and the laboratory procedures in medicinal chemistry, biochemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

As used herein, "about" indicates a range of +/−10%. For example, "about 10 mg 4-MP" means a range of from 9.0 mg to 11.0 mg 4-MP.

As used herein, "ethanol intolerance," refers to a condition in which a subject experiences a symptom of acetaldehyde accumulation accompanying ethanol consumption. Symptoms of ethanol intolerance, or acetaldehyde accumulation, may include, but are not limited to, flushing, elevated heart rate, palpitations, hypotension, nausea, dizziness, headache, vomiting, diarrhea, upset stomach, ataxia, or confused consciousness. See, for example, Ward et al., *Alcohol and Alcoholism* 1994, 29, 433-438.

As used herein, "acetaldehyde accumulation" refers to the production of acetaldehyde in a subject that has consumed ethanol.

The term "effective amount" as used herein refers to the amount of 4-MP, or physiologically acceptable salt thereof, that is sufficient to produce a desirable or beneficial effect when contacted, for example, to an alcohol dehydrogenase enzyme, or, as another example, when administered to a subject. In certain embodiments, the "effective amount" is, for example, the amount to prevent, reduce or ameliorate a symptom associated with acetaldehyde accumulation in a subject accompanying ethanol consumption, or to reduce the likelihood or risk in a subject for a disease or disorder caused by consumption of ethanol.

As used herein, the term "dose" or "dosage" refers to the amount of 4-MP that an subject takes or is administered at one time. As used herein, the term "unit dosage" or "dosage unit" refers to a physically discrete unit, such as a tablet or capsule, suitable as a unitary dosage for a subject. The dosage unit comprises 4-MP in association with at least one excipient. By way of example, an 100 mg 4-MP dose refers to the amount of 4-MP a subject can take at one time, where the dose can be divided into two 50 mg dosage units, for example, two 50 mg 4-MP capsules.

As defined herein, where the mass of 4-MP is specified, for example, "10 mg 4-MP," that amount refers to the equivalent mass of 4-MP in its free base form. Thus, for example, if 10 mg 4-MP in a given salt form is to be administered in a formulation disclosed herein, one of skill in the art can make the necessary conversion using the molecular masses of the salt form of 4-MP and of the free base form of 4-MP to determine the actual mass of that salt form of 4-MP necessary to obtain the equivalent mass of 10 mg 4-MP in its free base form. As another example, if 10 mg 4-MP in a free base form is to be administered in a formulation disclosed herein, then no conversion is necessary.

The term "physiologically acceptable salt" or "acceptable salt form," as used herein, refers to the relatively nontoxic, inorganic and organic acid addition salts of compounds of the invention.

The term "room temperature," as used herein, refers to 25° C.±2° C. Typically, experiments as described herein are performed at room temperature and at 60%±5% relative humidity, unless otherwise stated.

As used herein, a "stable formulation" refers to a formulation which displays physical stability and/or chemical stability under storage conditions. Unless otherwise indicated, storage conditions are intended to cover those conditions in which pharmaceutical formulations are typically stored, and may include, for example, temperatures of up to about 25° C.; up to about 26° C.; up to about 27° C.; up to about 28° C.; up to about 29° C.; up to about 30° C.; up to about 31° C.; up to about 32° C.; up to about 33° C.; up to about 34° C.; up to about 35° C.; up to about 36° C.; up to about 37° C.; up to about 39° C.; or up to about 40° C.; relative humidities of up to about 10%; up to about 15%; up to about 20%; up to about 25%; up to about 30%; up to about 35%; up to about 40%; up to about 45%; up to about 50%; up to about 55%; up to about 60%; up to about 65%; up to about 70%; up to about 75%; up to about 80%; up to about 85%; up to about 90%; up to about 95%; or up to about 100%; and other conditions as specified.

As used herein, "chemical stability" of a formulation refers to the chemical stability of the active pharmaceutical unit (i.e., 4-MP) in a unit dosage form of the formulation, for example, a tablet or capsule of the formulation. Typically, chemical stability is evaluated through assaying the content of the active pharmaceutical unit in the formulation. Typically, a chemically stable formulation is one which displays limited degradation or loss of potency of the active pharmaceutical ingredient, or which displays limited loss of content of the active pharmaceutical ingredient, upon storage. Typical formulations provided herein will retain at least about 99%, at least about 98%, at least about 97%, at least about 96%, at least about 95%, at least about 94%, at least about 93%, at least about 92%, at least about 91%, or at least about 90% content of their active pharmaceutical ingredient upon storage for 8 months or more at room temperature and at relative humidities of up to about 60%±5%.

As used herein, "physical stability" of a formulation refers to the physical integrity of a unit dosage form of the formulation, for example, a tablet or capsule of the formulation. Typically, physical stability is evaluated through a visual inspection of the physical appearance of the unit dosage form. The physical appearance of the unit dosage form may include such physical characteristics as form, color, shape, odor, surface texture, and presence or absence of physical flaws, including the presence or absence of breaks or tears in the unit dosage form. Where the unit dosage form is a capsule, a physically stable formulation is typically one in which the capsule displays no deformity, breakage, or leakage of capsule contents. Typical formulations provided herein will be physically stable upon storage for 8 months or more at room temperature and at relative humidities of up to about 60%±5%.

The term "subject" refers to animals such as mammals, including, but not limited to, primates (e.g., humans), monkeys, cattle, sheep, goats, horses, dogs, cats, rabbits, pigs, deer, bear, rats, mice and the like. In preferable embodiments, the subject is a human.

The term "symptom" as used herein refers to a physical condition which indicates a particular illness or disorder (e.g., *Longman Dictionary of Contemporary English,* 1995, Third Edition) detectable by the subject suffering from a particular disease or disorder or detectable by a person other than the subject without verbal information from said subject.

The term "treat," "treating" or "treatment," as used herein, refers to a method of alleviating or abrogating a disorder and/or its attendant symptoms.

5. DETAILED DESCRIPTION OF THE INVENTION

Provided herein are storage stable formulations of 4-methylpyrazole (4-MP). In certain embodiments, the formulations are in a unit dosage form suitable for oral administration in a human. In certain embodiments, the formulations are in solid form.

5.1 Formulations

In one aspect, provided herein are formulations comprising 4-MP, or a physiologically acceptable salt form thereof.

4-Methylpyrazole (4-MP, also known as fomepizole) is commercially available from chemical suppliers, including, for example, Sigma Aldrich (St. Louis, Mo.), and can also be synthesized easily in commercially viable quantities of pharmaceutical grade.

In certain embodiments, the formulation comprises the free base of 4-MP. In certain embodiments, the formulation comprises a physiologically acceptable salt of 4-MP, for example, a hydrochloride salt of 4-MP.

In certain embodiments, the formulations comprise 4-MP, or a physiologically acceptable salt form thereof, and an excipient.

In certain embodiments, the excipient is a liquid.

In certain embodiments, the excipient is a solid.

In certain embodiments, the excipient is a solid at temperatures of up to about 25° C.; up to about 26° C.; up to about 27° C.; up to about 28° C.; up to about 29° C.; up to about 30° C.; up to about 31° C.; up to about 32° C.; up to about 33° C.; up to about 34° C.; up to about 35° C.; up to about 36° C.; up to about 37° C.; up to about 39° C.; or up to about 40° C.

In certain embodiments, the excipient is a solid at temperatures from at least 25° C. to up to about 40° C.; from at least 26° C. to up to about 40° C.; from at least 27° C. to up to about 40° C.; from at least 28° C. to up to about 40° C.; from at least 29° C. to up to about 40° C.; from at least 25° C. to up to about 30° C.; from at least 25° C. to up to about 35° C.; from at least 30° C. to up to about 35° C.; from at least 30° C. to up to about 40° C.; or from at least 35° C. to up to about 40° C.

In certain embodiments, the excipient is glycerine.

In certain embodiments, the excipient is a medium chain triglyceride, for example, a caprylic/capric triglyceride. In certain embodiments, the excipient is a miglyol, for example, Miglyol 812.

In certain embodiments, the excipient is a polyethylene glycol. Polyethylene glycols are typically used as excipients in pharmaceutical formulations. See, for example, Remington's *The Science and Practice of Pharmacy*, 2005, 21$^{st}$ ed.

In certain embodiments, the polyethylene glycol comprises a branched or a straight chain.

In certain embodiments, the polyethylene glycol has a total weight average molecular weight of from about 400 to about 40,000; from about 600 to about 40,000; from about 600 to about 30,000; from about 800 to about 30,000; from about 600 to about 20,000; from about 800 to about 20,000; from about 1000 to about 20,000; from about 1500 to about 20,000; from about 3000 to about 20,000; from about 3000 to about 10,000; from about 4000 to about 20,000; from about 4000 to about 10,000; from about 5000 to about 10,000; from about 4000 to about 9000; from about 5000 to about 9000; from about 6000 to about 9000; about 6000; or about 8000.

In certain embodiments, the excipient is selected from the group consisting of Polyethylene Glycol 400 (PEG 400), Polyethylene Glycol 600 (PEG 600), Polyethylene Glycol 800 (PEG 800), Polyethylene Glycol 1000 (PEG 1000), Polyethylene Glycol 1500 (PEG 1500), Polyethylene Glycol 2000 (PEG 2000), Polyethylene Glycol 3000 (PEG 3000), Polyethylene Glycol 4000 (PEG 4000), Polyethylene Glycol 6000 (PEG 6000), Polyethylene Glycol 8000 (PEG 8000), Polyethylene Glycol 9000 (PEG 9000), Polyethylene Glycol 10,000 (PEG 10,000), Polyethylene Glycol 20,000 (PEG 20,000), Polyethylene Glycol 30,000 (PEG 30,000), Polyethylene Glycol 40,000 (PEG 40,000), and a combination thereof.

In certain embodiments, the excipient is a high molecular weight polyethylene glycol, for example, Polyethylene Glycol 8000 (PEG 8000).

As opposed to other excipients, high molecular weight polyethylene glycols are found to be particularly suitable for the formulations disclosed herein.

In certain embodiments, the excipient is PEG 6000 or PEG 8000.

In certain embodiments, the excipient is PEG 6000.

In certain embodiments, the excipient is PEG 8000.

Certain excipients, as demonstrated herein, contribute to the chemical and physical stability of the formulations provided herein, including improved chemical and physical stability under storage conditions. Without intending to be bound by any particular theory, it is believed that these excipients induce a solid-state phase transition in the formulation, where the solid phase exhibits improved chemical and physical stability compared to the liquid phase of the formulation.

In certain embodiments, the formulations are in a solid form.

In certain embodiments, the formulations when in solid form comprise about 2% to about 60% wt/wt % of 4-MP, or a physiologically acceptable salt form thereof. In certain embodiments, the formulations when in solid form comprise about 3% to about 50% wt/wt % of 4-MP, or a physiologically acceptable salt form thereof. In certain embodiments, the formulations when in solid form comprise about 3% to about 40% wt/wt % of 4-MP, or a physiologically acceptable salt form thereof. In certain embodiments, the formulations when in solid form comprise about 3% to about 5%, about 5% to about 15%, about 10% to about 20%, about 15% to about 30%, or about 25% to about 50 wt/wt % of 4-MP, or a physiologically acceptable salt form thereof.

In certain embodiments, the formulations are in a solid form when stored at temperatures of up to about 40° C. and at relative humidities of up to about 95% for at least 8 months or more.

In certain embodiments, the formulations are in a solid form at temperatures of up to about 25° C.; up to about 26° C.; up to about 27° C.; up to about 28° C.; up to about 29° C.; up to about 30° C.; up to about 31° C.; up to about 32° C.; up to about 33° C.; up to about 34° C.; up to about 35° C.; up to about 36° C.; up to about 37° C.; up to about 39° C.; or up to about 40° C.

In certain embodiments, the formulations are in a solid form at temperatures from at least 25° C. to up to about 40° C.; from at least 26° C. to up to about 40° C.; from at least 27° C. to up to about 40° C.; from at least 28° C. to up to about 40° C.; from at least 29° C. to up to about 40° C.; from at least 25° C. to up to about 30° C.; from at least 25° C. to up to about 35° C.; from at least 30° C. to up to about 35° C.; from at least 30° C. to up to about 40° C.; or from at least 35° C. to up to about 40° C.

In certain embodiments, the formulations are in a solid form at temperatures of up to about 40° C.; and at relative humidities of up to about 10%; up to about 15%; up to about 20%; up to about 25%; up to about 30%; up to about 35%; up to about 40%; up to about 45%; up to about 50%; up to about 55%; up to about 60%; up to about 65%; up to about 70%; up to about 75%; up to about 80%; up to about 85%; up to about 90%; up to about 95%; or up to about 100%.

In certain embodiments, the formulations are in a solid form at temperatures from at least 25° C. to up to about 40° C.; and at relative humidities of about 0% to about 10%; about 10% to about 20%; about 20% to about 30%; about 30% to about 40%; about 40% to about 50%; about 50% to about 60%; about 60% to about 70%; about 70% to about 80%; about 80% to about 90%; or about 90% to about 100%.

In certain embodiments, the formulations are in a solid form when stored at room temperature for 6 months or more; 8 months or more; 12 months or more; 18 months or more; 24 months or more; or 36 months or more. In certain embodiments, the formulations are in a solid form when stored at room temperature for 8 months or more.

In certain embodiments, the formulations are in a solid form when stored at room temperature and at relative humidities of up to about 60%±5% for 6 months or more; 8 months or more; 12 months or more; 18 months or more; 24 months or more; or 36 months or more. In certain embodiments, the formulations are in a solid form when stored at room temperature and at relative humidities of up to about 60%±5% for 8 months or more.

In certain embodiments, the formulations are in a solid form when stored at temperatures of up to about 40° C. for 6 months or more; 8 months or more; 12 months or more; 18 months or more; 24 months or more; or 36 months or more. In certain embodiments, the formulations are in a solid form when stored at temperatures of up to about 40° C. for 8 months or more.

In certain embodiments, the formulations are in a solid form when stored at temperatures of up to about 40° C. and at relative humidities of up to about 60%±5% for 6 months or more; 8 months or more; 12 months or more; 18 months or more; 24 months or more; or 36 months or more. In certain embodiments, the formulations are in a solid form when stored at temperatures of up to about 40° C. and at relative humidities up to about 60%±5% for 8 months or more.

In certain embodiments, the formulations are physically and/or chemically stable when stored at temperatures of up to about 40° C. and at relative humidities of up to about 95% for at least 8 months or more.

In certain embodiments, the formulations are physically and/or chemically stable when stored at room temperature for 6 months or more; 8 months or more; 12 months or more; 18 months or more; 24 months or more; or 36 months or more. In certain embodiments, the formulations are physically and/or chemically stable when stored at room temperature for 8 months or more.

In certain embodiments, the formulations are physically and/or chemically stable when stored at room temperature and at relative humidities of up to about 60%±5% for 6 months or more; 8 months or more; 12 months or more; 18 months or more; 24 months or more; or 36 months or more. In certain embodiments, the formulations are physically and/or chemically stable when stored at room temperature and at relative humidities of up to about 60%±5% for 8 months or more.

In certain embodiments, the formulations are physically and/or chemically stable when stored at temperatures of up to about 40° C. for 6 months or more; 8 months or more; 12 months or more; 18 months or more; 24 months or more; or 36 months or more. In certain embodiments, the formulations are physically and/or chemically stable when stored at temperatures of up to about 40° C. for 8 months or more.

In certain embodiments, the formulations are physically and/or chemically stable when stored at temperatures of up to about 40° C. and at relative humidities of up to about 60%±5% for 6 months or more; 8 months or more; 12 months or more; 18 months or more; 24 months or more; or 36 months or more. In certain embodiments, the formulations are physically and/or chemically stable when stored at temperatures of up to about 40° C. and at relative humidities up to about 60%±5% for 8 months or more.

In certain embodiments, the formulations are provided in the unit dosage form of a capsule and are physically stable. For example, in certain embodiments, the capsule displays no deformity, breakage, or leakage of contents when stored at room temperature for 6 months or more; 8 months or more; 12 months or more; 18 months or more; 24 months or more; or 36 months or more. In certain embodiments, the capsule displays no deformity, breakage, or leakage of contents when stored at room temperature for 8 months or more.

In certain embodiments, the capsule displays no deformity, breakage, or leakage of contents when stored at room temperature and at relative humidities of up to about 60%±5% for 6 months or more; 8 months or more; 12 months or more; 18 months or more; 24 months or more; or 36 months or more. In certain embodiments, the capsule displays no deformity, breakage, or leakage of contents when stored at room temperature and at relative humidities of up to about 60%±5% for 8 months or more.

In certain embodiments, the capsule displays no deformity, breakage, or leakage of contents when stored at temperatures of up to about 40° C. for 6 months or more; 8 months or more; 12 months or more; 18 months or more; 24 months or more; or 36 months or more. In certain embodiments, the capsule displays no deformity, breakage, or leakage of contents when stored at up to about 40° C. for 8 months or more.

In certain embodiments, the capsule displays no deformity, breakage, or leakage of contents when stored at temperatures of up to about 40° C. and at relative humidities of up to about 60%±5% for 6 months or more; 8 months or more; 12 months or more; 18 months or more; 24 months or more; or 36 months or more. In certain embodiments, the capsule displays no deformity, breakage, or leakage of contents when stored at temperatures of up to about 40° C. and relative humidities of up to about 60%±5% for 8 months or more.

In certain embodiments, the formulations are provided in the unit dosage form of a capsule and are chemically stable. For example, in certain embodiments, the capsule retains at least about 90% content of 4-MP when stored at room temperature for 6 months or more; 8 months or more; 12 months or more; 18 months or more; 24 months or more; or 36 months or more. In certain embodiments, the capsule retains at least about 99%, at least about 98%, at least about 97%, at least about 96%, at least about 95%, at least about 94%, at least about 93%, at least about 92%, at least about 91%, or at least about 90% content of 4-MP when stored at room temperature for 8 months or more.

In certain embodiments, the capsule retains at least about 90% content of 4-MP when stored at room temperature and at relative humidities of up to about 60%±5% for 6 months or more; 8 months or more; 12 months or more; 18 months or more; 24 months or more; or 36 months or more. In certain embodiments, the capsule retains at least about 99%, at least about 98%, at least about 97%, at least about 96%, at least about 95%, at least about 94%, at least about 93%, at least about 92%, at least about 91%, or at least about 90% content of 4-MP when stored at room temperature and at relative humidities of up to about 60%±5% for 8 months or more.

In certain embodiments, the capsule retains at least about 90% content of 4-MP when stored at temperatures of up to about 40° C. for 6 months or more; 8 months or more; 12 months or more; 18 months or more; 24 months or more; or 36 months or more. In certain embodiments, the capsule retains at least about 99%, at least about 98%, at least about 97%, at least about 96%, at least about 95%, at least about 94%, at least about 93%, at least about 92%, at least about 91%, or at least about 90% content of 4-MP when stored at temperatures of up to about 40° C. for 8 months or more.

In certain embodiments, the capsule retains at least about 90% content of 4-MP when stored at temperatures of up to about 40° C. and at relative humidities of up to about 60%±5% for 6 months or more; 8 months or more; 12 months or more; 18 months or more; 24 months or more; or 36 months or more. In certain embodiments, the capsule retains at least about 99%, at least about 98%, at least about 97%, at least about 96%, at least about 95%, at least about 94%, at least about 93%, at least about 92%, at least about 91%, or at least about 90% content of 4-MP when stored at temperatures of up to about 40° C. and at relative humidities of up to about 60%±5% for 8 months or more.

The formulations provided herein may further comprise one or more additional excipients. In certain embodiments, the one or more additional excipients may be selected from the group consisting of binders, fillers, diluents, glidants, lubricants, surfactants, emulsifying agents, disintegrants, coatings, flavors, colors, sweetening agents, preservatives, sorbents, and any other additive known to one of skill in the art.

Suitable binders may include, but are not limited to, hydroxypropyl cellulose, hydroxypropyl methyl cellulose, microcrystalline cellulose, polyvinylpyrrolidone, polyvinylpolypyrrolidone, polyethylene glycol, gum tragacanth, gelatin, and the like.

Suitable fillers and/or diluents may include, but are not limited to, lactose, glucose, sucrose, mannitol, sorbitol, calcium carbonate, calcium sulfate, calcium phosphate, hydroxypropyl cellulose, microcrystalline cellulose, silicified microcrystalline cellulose, water, ethanol, polyethylene glycol, propylene glycol, glycerol, starch, polyvinylpyrrolidone, magnesium stearate, magnesium metasilicate aluminate, and the like.

Suitable glidants may include, but are not limited to, silicon dioxide, colloidal silicon dioxide, talc, magnesium carbonate, and the like.

Suitable lubricants may include, but are not limited to, stearic acid; stearic acid metal salts such as calcium stearate or magnesium stearate; talc; colloidal silica; waxes such as beeswax; sulfates such as sodium sulfate; glycol; lauryl sulfates such as sodium lauryl sulfate or magnesium lauryl sulfate; silicates such as silicic anhydride or silicate hydrate; and the like.

Suitable surfactants may include, but are not limited to, anionic surfactants such as sodium dodecyl sulfate; cationic surfactants such as hexadecyl trimethyl ammonium bromide; amphoteric surfactants such as cocamidopropyl betaine; non-ionic surfactants such as propylene glycol monocaprylate (Capryol 90®) or diethylene glycol monoethyl ether (Transcutol®); and the like.

Suitable disintegrants may include, but are not limited to, cellulose derivatives such as low-substituted hydroxypropyl cellulose, carboxymethyl cellulose, calcium carboxymethyl cellulose or internally crosslinked sodium carboxymethyl cellulose; crosslinked polyvinylpyrrolidone; and chemically modified starches/celluloses such as carboxymethyl starch, sodium carboxymethyl starch, sodium starch glycolate, pregelatinised starch or croscarmellose sodium; and the like.

Suitable coatings may include, but are not limited to, hydroxy propylmethylcellulose (HPMC), gelatin, and the like.

Suitable preservatives may include, but are not limited to, cysteine, methionine, citric acid, sodium citrate, methyl paraben, propyl paraben, and the like.

5.2 Unit Dosages

In certain embodiments, the formulations provided herein are provided as a unit dosage.

The unit dosage may be produced using any commonly used method well known to one of skill in the art. Examples of suitable methods include those disclosed in, for example, Ansel et at, *Pharmaceutical Dosage Forms and Drug Delivery Systems*, $6^{th}$ ed., 1995, Williams & Wilkins, Baltimore Md. For example, the unit dosage forms provided herein may be prepared by mixing particles of 4-MP, or a physiologically acceptable salt form thereof, and one or more excipients to form a bulk blend. When the bulk blend is sufficiently mixed so as to be homogenous, the composition may be readily subdivided into unit dosages, for example, tablets, pills, capsules, caplets, and the like. In the unit dosage, the 4-MP, or a physiologically acceptable salt form thereof, is included in an effective amount sufficient to produce the desired effect, for example, the desired effect of treating ethanol intolerance in the subject.

5.2.1. Unit Dosage Forms

In certain embodiments, the unit dosage is in the form of a tablet.

Tablets may be prepared using any tableting technique known to one of skill in the art. For example, tablets may be prepared by a direct compression method, wherein the bulk blend is transferred directly to a compression machine for pressing into a tablet. Other conventional methods such as wet granulation or dry granulation may also be used. See, for example, Ansel et al., *Pharmaceutical Dosage Forms and Drug Delivery Systems*, 1995, $6^{th}$ ed., Williams & Wilkins, Baltimore Md., pp. 182-222.

In certain embodiments, the unit dosage is in the form of a capsule.

Capsules may be prepared using any capsule-filling technique known to one of skill in the art. For example, capsules may be prepared by transferring the bulk blend directly to a capsule filling and sealing machine, as described in, for example, U.S. Pat. Nos. 6,834,475 and 7,082,738. See also, for example, Ansel et al., *Pharmaceutical Dosage Forms and Drug Delivery Systems*, 1995, $6^{th}$ ed., Williams & Wilkins, Baltimore Md., pp. 164-182.

The capsules may be comprised of gelatin, plasticized gelatin, hydroxypropylmethylcellulose (HPMC), starch or agar, or any other material known to one of skill in the art.

In certain embodiments, the capsule comprises gelatin. In certain embodiments, the capsule comprises soft gelatin. In certain embodiments, the capsule comprises hard gelatin.

Plasticizers may be added to the capsule material to increase the flexibility and strength and may be selected from glycerin, propylene glycol, polyethylene glycol, triethyl citrate, acetyl triethyl citrate, diethyl phthalate, dibutyl phthalate, dibutyl sebacate, or mixtures thereof, or any other material or mixture known to one of skill in the art. The plasticizer may be present in an amount ranging from 0.1% to 30% by weight of the capsule.

The capsules may be sized to hold the desired amount of the formulation, typically up to about 0.50 ml of formulation. Preferably, the size of any particular capsule described herein will correspond to a conventional capsule size, e.g. Size Nos. 00, 0, 1, 2, 3, 4, 5, and the like. See, for example, Remington's *The Science and Practice of Pharmacy*, 2005, $21^{st}$ ed.

The tablets and capsules may also be coated with an enteric coating, alone or in addition to another coating. See, for example, Remington's *The Science and Practice of Pharmacy*, 2005, $21^{st}$ ed.

Materials suitable for use in the enteric coating include hydroxypropyl methylcellulose, hydroxyethyl cellulose, hydroxypropyl cellulose, methylcellulose, ethylcellulose, acrylic acid methacrylic acid ester copolymer, or a mixture thereof.

Additional materials suitable for use in the enteric coating include phthalates including hydroxypropyl methylcellulose phthalate, hydroxyethyl cellulose phthalate, hydroxypropyl cellulose phthalate, methylcellulose phthalate, ethylcellulose phthalate, and cellulose acetate phthalate.

The tablets and capsules may additionally be coated with a controlled release coating, which is compatible with the other components of the enteric coating. The controlled release coating may comprise a hydrophobic controlled release material selected from an alkylcellulose, an acrylic polymer, or mixtures thereof.

The controlled release coatings may also include a plasticizer such as those described herein.

5.2.2. Amounts of 4-MP

In certain embodiments, the unit dosages provided herein comprise different amounts of 4-MP.

In certain embodiments, the unit dosages comprise about 0.05 mg; about 0.1 mg; about 0.5 mg; about 1.0 mg; about 1.5 mg; about 2.0 mg; about 2.5 mg; about 3.0 mg; about 3.5 mg; about 4.0 mg; about 4.5 mg; or about 5.0 mg 4-MP.

In certain embodiments, the unit dosages comprise about 5.0 mg; about 6.0 mg; about 7.0 mg; about 8.0 mg; about 9.0 mg; about 10.0 mg; about 15.0 mg; about 20.0 mg; or about 50.0 mg 4-MP.

In certain embodiments, the unit dosages comprise about 50.0 mg; about 60.0 mg; about 70.0 mg; about 80.0 mg; about 90.0 mg; about 100.0 mg; about 150.0 mg; about 200.0 mg; or about 500.0 mg 4-MP.

In certain embodiments, the unit dosages comprise about 0.05 to about 5.0 mg; about 0.1 to about 5.0 mg; about 0.5 to about 5.0 mg; about 1.0 to about 5.0 mg; about 0.5 to about 4.0 mg; about 0.5 to about 3.0 mg; about 0.5 to about 2.0 mg; about 0.5 to about 1.0 mg; about 1.0 to about 2.0 mg; about 2.0 to about 3.0 mg; about 3.0 to about 4.0 mg; or about 4.0 to about 5.0 mg 4-MP.

In certain embodiments, the unit dosages comprise about 5.0 to about 50.0 mg; about 10.0 to about 50.0 mg; about 5.0 to about 6.0 mg; about 6.0 to about 7.0 mg; about 7.0 to about 8.0 mg; about 8.0 to about 9.0 mg; about 9.0 to about 10.0 mg; about 10.0 to about 15.0 mg; about 15.0 to about 20.0 mg; or about 20.0 to about 50.0 mg 4-MP.

In certain embodiments, the unit dosages comprise about 50.0 to about 500.0 mg; about 100.0 to about 500.0 mg; about 50.0 to about 60.0 mg; about 60.0 to about 70.0 mg; about 70.0 to about 80.0 mg; about 80.0 to about 90.0 mg; about 90.0 to about 100.0 mg; about 100.0 to about 150.0 mg; about 150.0 to about 200.0 mg; or about 200.0 to about 500.0 mg 4-MP.

5.3 Hard Gelatin Capsules

In another aspect, provided herein are hard gelatin capsules encapsulating 4-MP, or a physiologically acceptable salt form thereof, and an excipient.

In certain embodiments, the excipient in the capsule is a polyethylene glycol. In certain embodiments, the polyethylene glycol has a total weight average molecular weight of from about 5000 to about 10,000. In certain embodiments, the excipient in the capsule is PEG 6000 or PEG 8000.

In certain embodiments, the capsule retains physical integrity when stored at temperatures of up to about 55° C. for at least 8 months or more. In certain embodiments, the capsule retains physical integrity when stored at temperatures of up to about 40° C. and at relative humidities of up to about 95% for at least 8 months or more. In certain embodiments, the capsule retains physical integrity when stored at room temperature and at relative humidities of up to about 60%±5% for 8 months or more.

In certain embodiments, the contents of the capsule are in solid form. In certain embodiments, the contents of the capsule are in solid form at temperatures of up to about 40° C. and at relative humidities of up to about 95% for at least 8 months or more. In certain embodiments, the contents of the capsule are in solid form at room temperature and at relative humidities of up to about 60%±5% for 8 months or more.

5.4 Methods of Administration

In another aspect, provided herein are methods of administration of the formulations provided herein.

The formulations provided herein can be administered according to any technique known to one of skill in the art. In preferable embodiments, the subject can self-administer the formulation to himself or herself. In preferable embodiments, the formulation can be administered orally. When orally administered, the formulation can be in a solid form. When orally administered, the formulations can also be in a unit dosage form, for example, as in a tablet, capsule and the like, as provided herein.

The formulation can be administered alone or in combination with other substances or active agents. In some embodiments, a formulation and other ingredients, as described below, is administered.

In certain embodiments, the amount of 4-MP administered in the formulation can be between about 0.05 mg/kg to about 5.0 mg/kg. In certain embodiments, the amount of 4-MP administered in the formulation can be between about 0.1 mg/kg to about 5.0 mg/kg. In certain embodiments, the amount of 4-MP administered in the formulation can be between about 1.0 mg/kg to about 5.0 mg/kg. In certain embodiments, the amount of 4-MP administered in the formulation can be between about 0.05 mg/kg to 0.1 mg/kg. In certain embodiments, the amount of 4-MP administered in the formulation can be between about 0.1 mg/kg to 1.0 mg/kg. In certain embodiments, the amount of 4-MP administered in the formulation can be between about 1.0 mg/kg to 2.0 mg/kg. As will be understood by one of skill in the art, the amounts of 4-MP to be administered in the formulation, as described herein, are based on the body mass of the subject, expressed in kilograms. In some embodiments, 0.05 mg/kg, about 0.1 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, or about 5.0 mg/kg of 4-MP are administered to the subject in the formulation. In certain embodiments, the amount of 4-MP administered in the formulation can be in the range between about 0.05 mg/kg to about 0.1 mg/kg; between about 0.1 mg/kg to about 1.0 mg/kg; or between about 1.0 mg/kg to about 2.0 mg/kg.

In certain embodiments, the formulations provided herein, when administered to a subject, can be effective to reduce or inhibit the ethanol-oxidizing activity of alcohol dehydrogenase (ADH) in the subject.

In certain embodiments, the formulations provided herein are suitable for administration to subjects wishing to reduce or ameliorate a symptom of ethanol intolerance or acetaldehyde accumulation. In certain embodiments, the subject has reduced or absent aldehyde dehydrogenase subtype 2 (ALDH2) activity, as described in Goedde et al., *Hum. Genet.* 1992, 88, 344-346, and Xiao et al., *J. Clin. Invest.* 1995, 96, 2180-2186. Symptoms of ethanol intolerance, or acetaldehyde accumulation, may include, but are not limited to, flushing, elevated heart rate, palpitations, hypotension, nausea, dizziness, headache, vomiting, diarrhea, upset stomach, ataxia, or confused consciousness. See, for example, Ward et al., *Alcohol and Alcoholism* 1994, 29, 433-438. In certain embodiments, the subject is a human.

In certain embodiments, the formulation can be administered before the subject has consumed ethanol. In certain embodiments, the formulation can be administered about one minute, about fifteen minutes, or about one hour before the subject consumes ethanol. In certain embodiments, the formulation can be orally administered about two hours to about fifteen minutes before the subject consumes ethanol.

In certain embodiments, the formulation can be administered concurrent with the consumption of ethanol. In certain embodiments, the formulation can be administered immediately before or after the consumption of ethanol. In certain embodiments, the formulation can be administered to a subject after the subject has consumed ethanol.

In certain embodiments, the amount of 4-MP, or physiologically acceptable salt thereof, administered in the formulation can be effective to reduce acetaldehyde accumulation by about 50% to about 60% in a subject as compared to when the formulation is not administered to the subject. In certain embodiments, the peak acetaldehyde accumulation can be effectively eliminated or reduced by about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, or about 5%.

In certain aspects, the present invention provides methods for preventing a disease associated with the long term use of ethanol in a subject. In general, diseases associated with the long term use of ethanol include, for example and without limitation, liver cirrhosis and cancer, for example, hepatocellular carcinoma, mouth cancer, stomach cancer, and esophageal cancer.

In certain preferable embodiments of methods provided for preventing a disease associated with the long term use of ethanol in a subject, 4-MP is administered prior to the consumption of ethanol by the subject. In some embodiments, 4-MP can be administered within about two hours before the subject consumes ethanol.

6. EXAMPLES

6.1 Experimental Methods

This section describes the experimental methods used to test the physical and/or chemical stability of the formulations provided herein.

All formulations studied were in the unit dosage form of a capsule.

Physical appearance of the capsules was evaluated by visual inspection. The capsules must be white opaque, intact with no leaking or deformity.

The content of 4-MP in each capsule was determined by RP-HPLC (Reversed Phase High Performance Liquid Chromatography). The contents of the capsule were solubilized in mobile phase (950 mL water/50 mL acetonitrile/2 mL triethylamine) and injected on a $C_8$ (150×4.6 mm) 5 µm column. The elution was monitored at 210 nm. The 4-MP content in the capsule was determined by comparing the peak area of a known standard. Purity and concentration of the standard solution were considered in the calculation.

Dissolution of 4-MP capsules was evaluated using filtered water as medium at 50 rpm. One capsule is placed in the dissolution medium and sampled at 10 minutes, 20 minutes, and 30 minutes. Each sample was analyzed using the chromatographic conditions specified in the Assay test method description.

Related substances were analyzed using a RP-HPLC method using a $C_{18}$ (150×4.6 mm) 5 µm column and a mobile phase comprised of 4 g Octanesulphonic acid sodium salt/4.14 g sodium dihydrogen orthophosphate monohydrate/800 mL water/150 mL methanol/50 mL acetonitrile, pH 3.0. The elution was monitored at 210 nm. The contents of the capsule were solubilized in mobile phase and injected on the column in addition to known related impurity standards. Any impurity ≥0.05% in the sample chromatogram was reported by retention time and % peak area of total peak area.

The water content of 4-MP drug product was determined using a Karl Fischer reagent per USP.

6.2 Effect of Capsule Material on Stability of Formulations

This example demonstrates effect of capsule material on the physical and chemical stability of the 4-MP formulations.

6.2.1. HMPC Capsules: Physical Stability

Hydroxypropylmethylcellulose (HPMC) capsules were tested for compatibility with the active pharmaceutical ingredient, 4-MP, and with certain excipients. Two excipients were studied in the HPMC capsules; Glycerin and Miglyol 812. The capsule tested was a Size 3 Opaque White HPMC Capsule supplied by Qualicaps®. Formulations #1-#3 prepared for this study are summarized in Table 1.

TABLE 1

Formulations to Study Effect of Capsule Material on Physical Stability - HPMC Capsules

| Ingredients | Formulation #1 (mg/cap)† | Formulation #2 (mg/cap) | Formulation #3 (mg/cap) |
|---|---|---|---|
| Glycerin | 140 | — | — |
| Miglyol 812 | — | 140 | — |
| 4-MP | 100 | 100 | 240 |
| Fill Weight | 240 | 240 | 240 |

†mg/cap = milligram per capsule
— = Not added

Filled capsules were placed in clear sealed glass vials in an upright position at 40° C. and at room temperature to test for chemical and physical stability. Capsules were not banded. Vials were sampled weekly for assay testing and were examined weekly for physical appearance.

The HMPC capsules of Formulations #1-#3 deformed and leaked after one week at room temperature. However, the capsules filled with placebo (glycerin or Miglyol 812 only) were physically intact after one week at 40° C.

This example demonstrates that certain formulations encapsulated in HPMC capsules are not physically stable, and therefore that HPMC is not a suitable capsule material for 4-MP or for certain formulations of 4-MP.

6.2.2. Hard Gelatin Capsules: Physical Stability

Hard gelatin capsules were tested for compatibility with 4-MP and various excipients. Two excipients were studied in the hard gelatin capsules; PEG 400 and Miglyol 812. The capsule tested was a Size 3 Opaque White Gelatin Capsule supplied by Qualicaps®. Formulations #4-#11 prepared for this study are summarized in Tables 2 and 3.

TABLE 2

Formulations to Study Effect of Capsule Material on Physical Stability - Hard Gelatin Capsules (10 mg 4-MP)

| Ingredients | Formulation #4 (mg/cap)† | Formulation #5 (mg/cap) | Formulation #6 (mg/cap) | Formulation #7 (mg/cap) |
|---|---|---|---|---|
| PEG 400 | 230 | — | 229.98 | — |
| Miglyol 812 | — | 230 | — | 229.98 |
| BHA* | — | — | 0.024 | 0.024 |
| 4-MP | 10 | 10 | 10 | 10 |
| Fill Weight | 240 | 240 | 240 | 240 |

†mg/cap = milligram per capsule
— = Not added
*Butylated Hydroxyanisole (BHA) was added as an antioxidant

TABLE 3

Formulations to Study Effect of Capsule Material on Physical Stability - Hard Gelatin Capsules (100 mg 4-MP)

| Ingredients | Formulation #8 (mg/cap)† | Formulation #9 (mg/cap) | Formulation #10 (mg/cap) | Formulation #11 (mg/cap) |
|---|---|---|---|---|
| PEG 400 | 140 | — | 139.98 | — |
| Miglyol 812 | — | 140 | — | 139.98 |
| BHA* | — | — | 0.024 | 0.024 |
| 4-MP | 100 | 100 | 100 | 100 |
| Fill Weight | 240 | 240 | 240 | 240 |

†mg/cap = milligram per capsule
— = Not added
*Butylated Hydroxyanisole (BHA) was added as an antioxidant Filled capsules were placed in clear sealed glass vials in an upright position at 40° C. and 55° C. for 1, 2 and 3 months and at room temperature for 3 and 6 months to test for chemical and physical stability. Capsules were banded with a clear gelatin solution. Vials were sampled monthly for assay testing and were examined monthly for physical appearance.

The hard gelatin capsules of Formulations #4-#11 displayed no deformation or leakage after five days at 40° C.

This example demonstrates that formulations encapsulated in hard gelatin capsules are physically stable versus those in HPMC capsules. These results demonstrate that hard gelatin capsules are suitable for a variety of formulations of 4-MP, even where those formulations are stored at relatively high temperatures (e.g., 55° C.).

6.2.3. Formulations in Hard Gelatin Capsules: Capsule Integrity

The chemical stability of the contents of the capsule of Formulation #9 (see Table 3) was tested over different storage conditions. Table 4 shows the assay results for Formulation #9 after 1-2 weeks at room temperature, 40° C. and 55° C. Assay results are provided as the amount of 4-MP per capsule (mg/cap) and the percentage of 4-MP remaining (% label claim) under the specified assay conditions, based on an original fill formulation of 100 mg 4-MP. According to Table 4, the contents of the capsule of Formulation #9 retain at least 97.1% of the amount of 4-MP after two weeks at room temperature, and 95.7% of the amount of 4-MP after two weeks at 40° C. Even at relatively high temperature of 55° C., Formulation #9 retains 91.6% of the amount of 4-MP after two weeks.

TABLE 4

Chemical Stability of Formulation - Assay Results for Hard Gelatin Capsules

| | Assay Results | | |
|---|---|---|---|
| Formulation # | mg/cap† | % label claim | Assay Conditions |
| Formulation #9 | 96.12 | 96.1 | 1 week @ RT |
| Formulation #9 | 97.04 | 97.0 | 1 week @ 40° C. |
| Formulation #9 | 93.97 | 94.0 | 1 week @ 55° C. |
| Formulation #9 | 97.13 | 97.1 | 2 weeks @ RT |
| Formulation #9 | 95.70 | 95.7 | 2 weeks @ 40° C. |
| Formulation #9 | 91.64 | 91.6 | 2 weeks @ 55° C. |

†mg/cap = milligram per capsule

This example demonstrates that hard gelatin capsules are particularly suitable for the formulations provided herein, preserving capsule integrity and protecting the contents of the capsule from degredation and leakage even at the relatively high temperature of 55° C.

6.3 Effect of Excipient on Stability of Formulations

This example illustrates the effect of excipient on the physical and chemical stabilities of the formulations provided herein.

6.3.1. Excipients Tested

The effect of excipient on the physical and chemical stability of the formulation in the hard gelatin capsule was tested. The capsule tested was a Size 3 Opaque White Gelatin Capsule supplied by Qualicaps®. Formulations #12-#17 prepared for this study are summarized in Table 5.

TABLE 5

Formulations to Study Effect of Excipient on Physical and Chemical Stability

| Ingredients | Formulation #12 (mg/cap)† | Formulation #13 (mg/cap) | Formulation #14 (mg/cap) | Formulation #15 (mg/cap) | Formulation #16 (mg/cap) | Formulation #17 (mg/cap) |
|---|---|---|---|---|---|---|
| PEG 400 | 238.4 | 148.4 | — | — | — | — |
| Miglyol 812 | — | — | 260 | 170 | — | — |
| PEG 8000 | — | — | — | — | 260 | 170 |
| 4-MP | 10 | 100 | 10 | 100 | 10 | 100 |
| Povide K-30 (3%) | 8.1 | 8.1 | — | — | — | — |
| Water | 13.5 | 13.5 | — | — | — | — |
| Fill Weight | 270 | 270 | 270 | 270 | 270 | 270 |

†mg/cap = milligram per capsule
— = Not added

Filled capsules were placed in clear sealed glass vials in an upright position at 40° C. for 1, 2 and 3 months and at room temperature for 3 and 8 months to test for chemical and physical stability. Capsules were banded with a clear gelatin solution. Vials were sampled monthly for assay testing and were examined monthly for physical appearance.

6.3.2. Effect of Excipient: Physical Stability

The effect of excipient on the physical stability of Formulations #12-#17 (see Table 5) is shown in Table 6. Use of PEG 400 as an excipient (Formulations #12 and #13) resulted in brittle capsules that were prone to leakage and breakage after three months at room temperature, and that were fused together after 8 months at room temperature. Similarly, use of Miglyol 812 as an excipient (Formulations #14 and #15) resulted in capsules that leaked after three months at room temperature, and that were fused together after 8 months at room temperature. PEG 8000 as an excipient (Formulations

16 and #17) resulted in intact capsules that conformed to desired appearance after 8 months at room temperature.

TABLE 6

Effect of Excipient on Physical Stability

| Formulation | Conditions | Observations |
|---|---|---|
| Formulation #12 | 3 months at RT and 40° C.; 8 months at RT | capsules leaking and breaking (3 months); capsules fusing (8 months) |
| Formulation #13 | 3 months at RT and 40° C.; 8 months at RT | capsules leaking and breaking (3 months); capsules fusing (8 months) |
| Formulation #14 | 3 months at RT and 40° C.; 8 months at RT | capsules leaking (3 months); capsules fusing (8 months) |
| Formulation #15 | 3 months at RT and 40° C.; 8 months at RT | capsules leaking (3 months); capsules fusing (8 months) |
| Formulation #16 | 8 months at RT | capsules intact and conforming to expected appearance |
| Formulation #17 | 8 months at RT | capsules intact and conforming to expected appearance |

This example demonstrates that formulations comprising the excipient PEG 8000 in a hard gelatin capsule are physically stable when stored at room temperature for 8 months or more.

6.3.3. Formulations Comprising PEG 8000: Chemical Stability

The contents of the capsules of Formulations #16 and #17, which included the excipient PEG 8000 (see Table 5), were tested for chemical stability.

Tables 7 and 8 shows assay results at time zero (t=0) and after 8 months at room temperature for Formulations #16 (10 mg 4-MP) and #17 (100 mg 4-MP), respectively. Assay results are provided as the amount of 4-MP per capsule (mg/cap) and the percentage of 4-MP remaining (% label claim) under the specified assay conditions, based on an original fill formulation of 10 or 100 mg 4-MP.

TABLE 7

Chemical Stability - Assay Results for Formulation #16

|  | Time 0 | 8 months RT |
|---|---|---|
| Assay % Label Claim | 100.7% | 93.3% |
| Dissolution |  |  |
| 10 min | 35% | 35% |
| 20 min | 81% | 75% |
| 30 min | 94% | 94% |
| Related Substances Report ≥0.05% | No reportable peaks | No reportable peaks |
| Water Content | Not performed | 0.89% |

TABLE 8

Chemical Stability - Assay Results for Formulation #17

|  | Time 0 | 8 months RT |
|---|---|---|
| Assay % Label Claim | 102.4% | 94.3% |
| Dissolution |  |  |
| 10 min | 87% | 84% |
| 20 min | 100% | 100% |
| 30 min | 100% | 101% |
| Related Substances Report ≥0.05% | No reportable peaks | No reportable peaks |
| Water Content | Not performed | 4.4% |

According to Tables 7 and 8, the contents of the capsule of Formulations #16 and #17 retained at least 93.3% and 94.3% of the amount of 4-MP, respectively, with no reportable peaks of related substances, after storage for 8 months at room temperature, which indicates limited or no degradation of 4-MP.

Further, according to Tables 7 and 8, there is no appreciable change in the dissolution profiles of Formulations #16 and #17 after storage for 8 months at room temperature.

This example demonstrates that formulations of 4-MP comprising the excipient PEG 8000 in a hard gelatin capsule are chemically stable, displaying little or no degredation of 4-MP, limited loss of content of 4-MP, and no appreciable change in dissolution profile, when stored at room temperature for 8 months or more.

Although the foregoing invention has been described in some detail by way of illustration and example for purposes of clarity of understanding, it will be apparent to one of skill in the art that certain changes and modifications will be practiced. Therefore, the description and examples should not be construed as limiting the scope of the invention, which is delineated by the appended claims.

All publications and patent applications cited in this specification are herein incorporated by reference as if each individual publication or patent application were specifically and individually indicated to be incorporated by reference.

The invention claimed is:

1. A solid formulation comprising:
(a) 4-methylpyrazole, or a physiologically acceptable salt form thereof; and
(b) an excipient, wherein the excipient is a polyethylene glycol having a total weight average molecular weight of from 5000 to 10,000 Da;
wherein the formulation is in a solid form at temperatures of from at least 25° C. to up to about 40° C.

2. The formulation of claim 1 wherein the formulation is in a solid form at temperatures of up to about 35° C.

3. The formulation of claim 1 wherein the formulation is in a solid form at temperatures of up to about 30° C.

4. The formulation of claim 1 wherein the excipient is PEG 8000.

5. The formulation of claim 1 wherein the formulation further comprises one or more additional excipients.

6. The formulation of claim 5 wherein the additional excipient is a surfactant.

7. The formulation of claim 5 wherein the additional excipient is selected from the group consisting of propylene glycol monocaprylate and diethylene glycol monoethyl ether.

8. The formulation of claim 1 wherein the formulation is provided as a unit dosage.

9. The formulation of claim 8 wherein the unit dosage is in the form of a tablet or capsule.

10. The formulation of claim 8 wherein the unit dosage is in the form of a capsule.

11. The formulation of claim 10 wherein the capsule comprises hard gelatin.

12. The formulation of claim 8 wherein the unit dosage comprises about 10 mg of 4-methylpyrazole.

13. The formulation of claim 8 wherein the unit dosage comprises about 100 mg of 4-methylpyrazole.

14. The formulation of claim 9 wherein the formulation is physically stable for 8 months or more at room temperature and at relative humidities of up to about 60%±5%.

15. The formulation of claim 9 wherein the formulation is chemically stable for 8 months or more at room temperature and at relative humidities of up to about 60%±5%.

16. A hard gelatin capsule encapsulating:
    (a) 4-methylpyrazole, or a physiologically acceptable salt form thereof; and
    (b) an excipient, wherein the excipient is a polyethylene glycol having a total weight average molecular weight of from 5000 to 10,000 Da;
    wherein the capsule retains physical integrity when stored for 8 months or more at room temperature and at relative humidities of up to about 60%±5%.

17. The hard gelatin capsule of claim 16 wherein the excipient is PEG 8000.

18. The hard gelatin capsule of claim 16 wherein the contents of the capsule are in a solid form.

19. The formulation of claim 1 wherein the formulation is suitable for oral administration in a human.

20. A method for treating or ameliorating a symptom of ethanol intolerance in a subject comprising the step of administering to the subject a formulation of claim 1.

\* \* \* \* \*